United States Patent [19]
Smith et al.

[11] Patent Number: 6,100,033
[45] Date of Patent: Aug. 8, 2000

[54] DIAGNOSTIC TEST FOR PRENATAL IDENTIFICATION OF DOWN'S SYNDROME AND MENTAL RETARDATION AND GENE THERAPY THEREFOR

[75] Inventors: Desmond J. Smith, Oakland; Edward M. Rubin, Berkeley, both of Calif.

[73] Assignee: The Regents of the University of California, Oakland, Calif.

[21] Appl. No.: 09/071,074

[22] Filed: Apr. 30, 1998

Related U.S. Application Data

[60] Provisional application No. 60/045,604, May 5, 1997.
[51] Int. Cl.⁷ .............................. C12Q 1/68; C07H 21/04
[52] U.S. Cl. ........................... 435/6; 435/91.1; 536/23.1; 536/24.31; 536/24.33
[58] Field of Search ................................ 536/23.5, 24.31, 536/24.33, 23.1; 435/320.1, 325, 6; 800/8

[56] References Cited

PUBLICATIONS

Song et al (Genomics 38:331–339, 1996.
Joo et al (J Biotechnol. 35(2–3):135–53, 1994.
Simpson et al, Ann. NY Acad. Sci. 731:1–8, 1994.

*Primary Examiner*—John L. LeGuyader
*Assistant Examiner*—Sumesh Kaushal
*Attorney, Agent, or Firm*—John W. Mahoney; David J. Aston; Paul R. Martin

[57] ABSTRACT

A a diagnostic test useful for prenatal identification of Down syndrome and mental retardation. A method for gene therapy for correction and treatment of Down syndrome. DYRK gene involved in the ability to learn. A method for diagnosing Down's syndrome and mental retardation and an assay therefor. A pharmaceutical composition for treatment of Down's syndrome mental retardation.

2 Claims, 16 Drawing Sheets

(5 of 16 Drawing Sheet(s) Filed in Color)

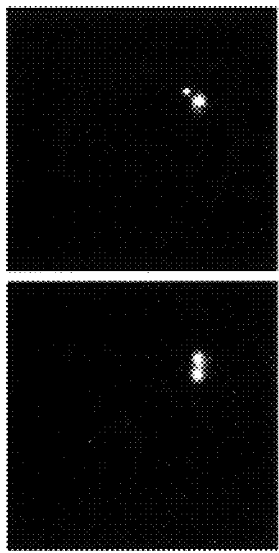
Fig. 2 F
Fig. 2 H
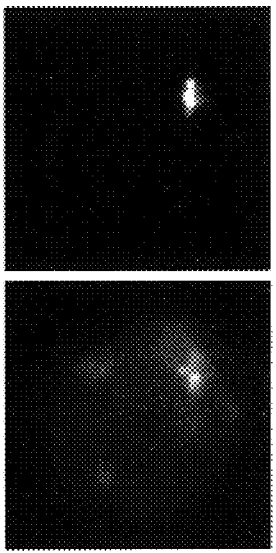
Fig. 2 G
Fig. 2 I
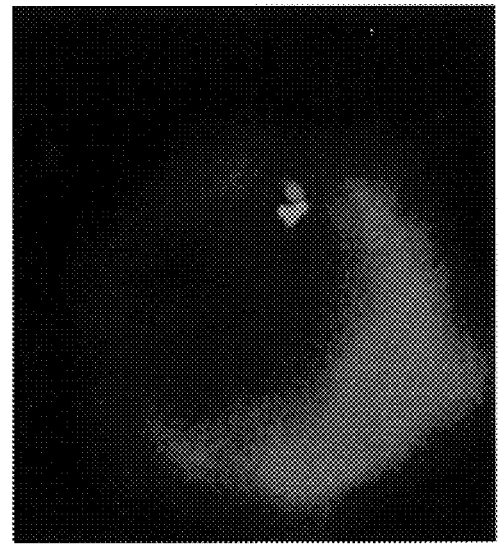
Fig. 2 J

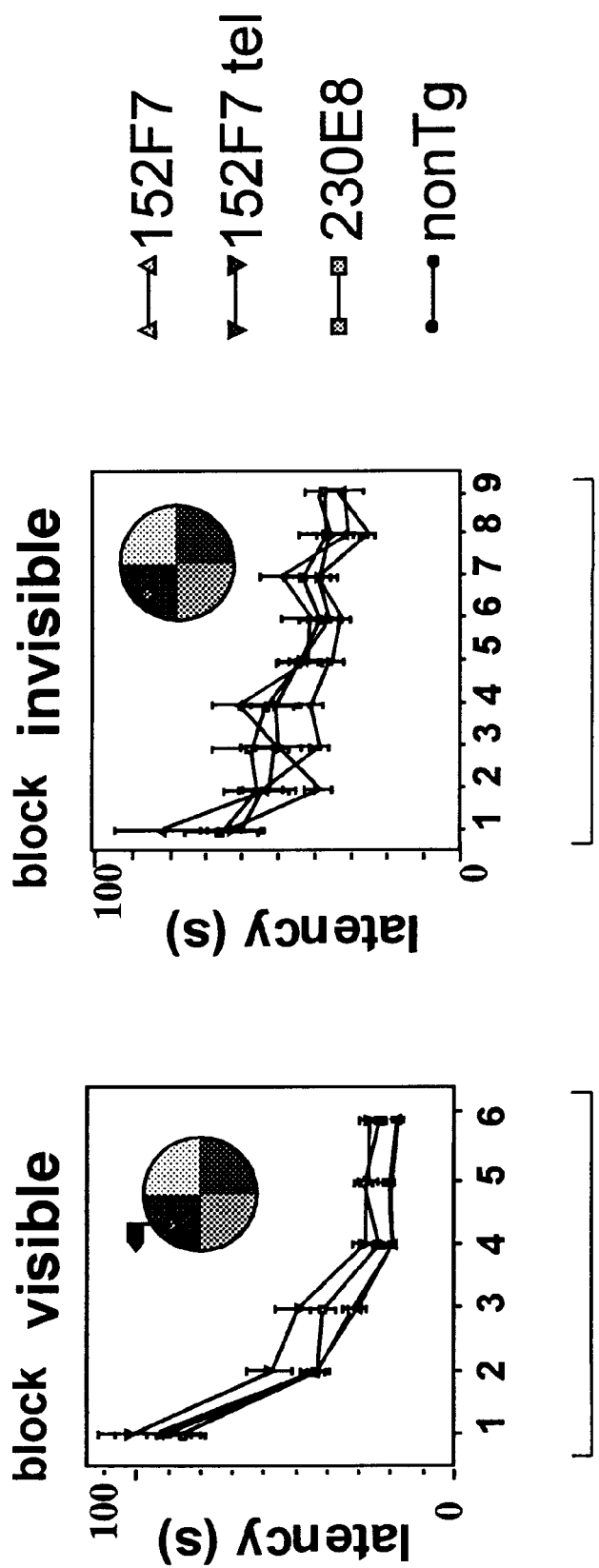

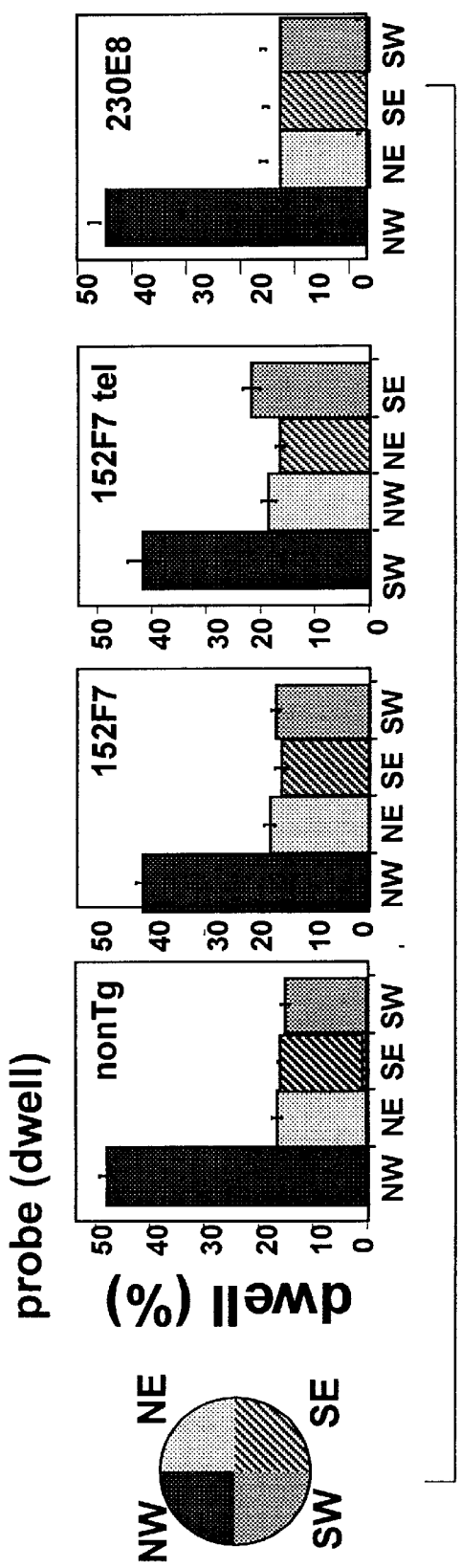
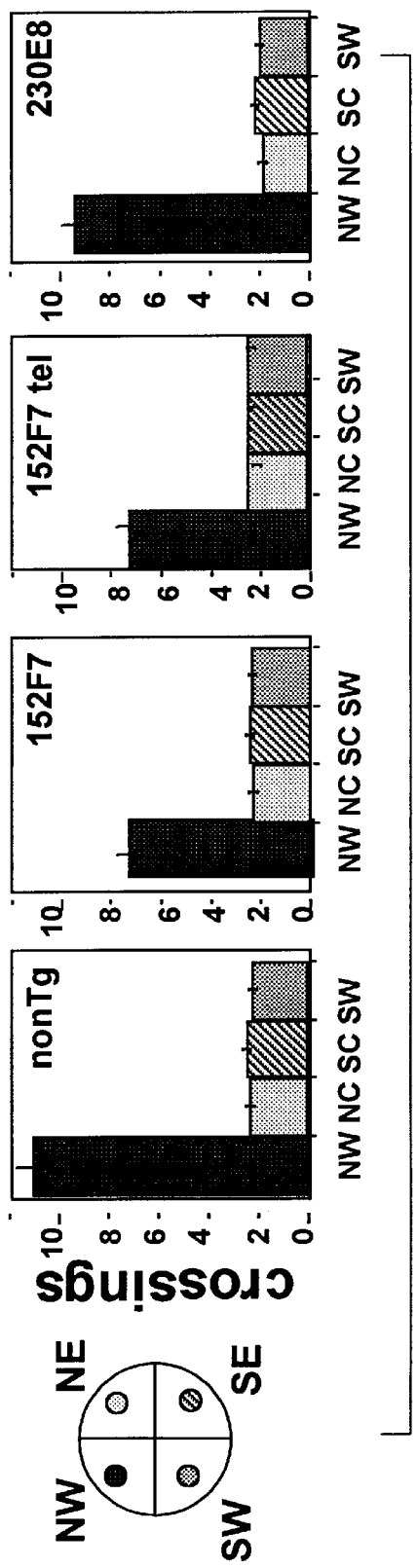
Fig. 3C
Fig. 3D

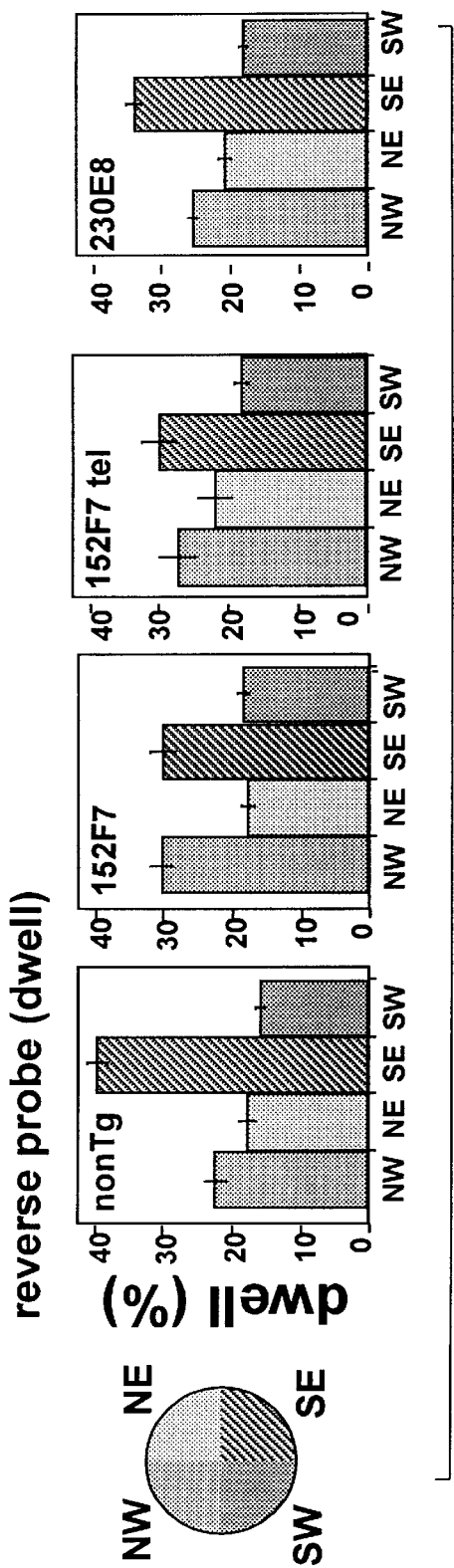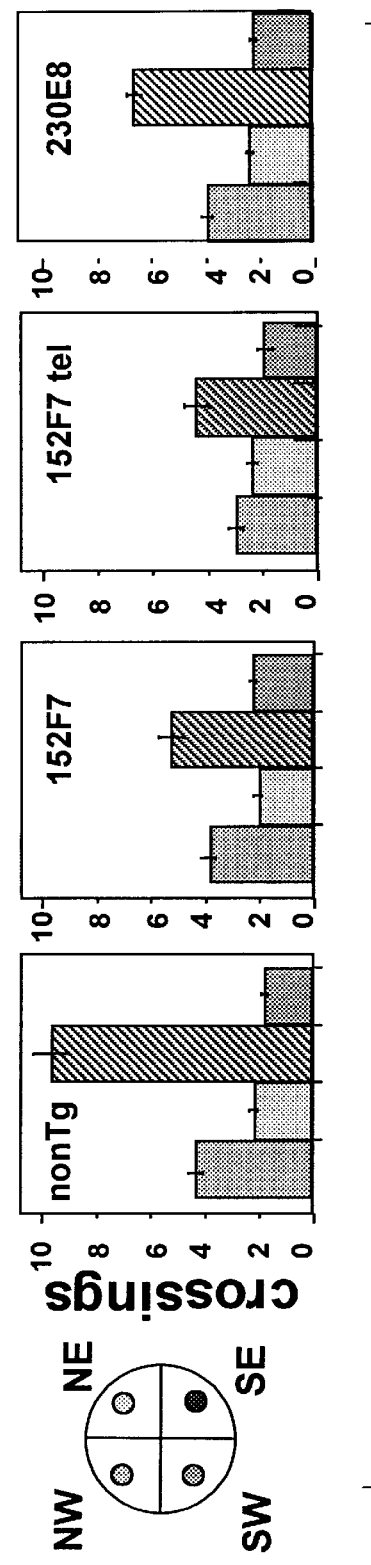
Fig. 4B
Fig. 4C

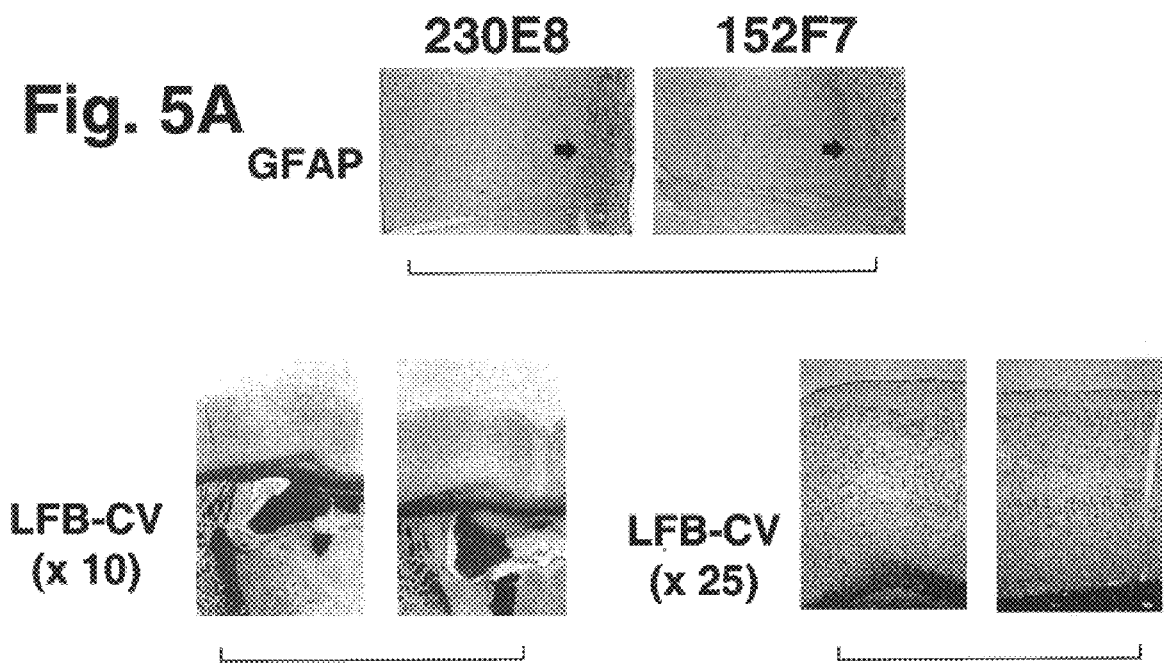

DIAGNOSTIC TEST FOR PRENATAL IDENTIFICATION OF DOWN'S SYNDROME AND MENTAL RETARDATION AND GENE THERAPY THEREFOR

This application claims priority to a Provisional Application Ser. No. 60/045,604, filed May 5, 1997.

REFERENCE TO GOVERNMENT INTEREST

This invention was made in the course of contract DE-AC03-76SF0098 between the United States Department of Energy and the University of California for the operation of Lawrence Berkeley Laboratory. The United States Government has certain rights to this invention.

BACKGROUND OF THE INVENTION

1. Field Of the Invention

This invention concerns a diagnostic test useful for prenatal identification of Down syndrome and mental retardation and a gene therapy for correction and treatment thereof. In particular, this invention concerns identification of DYRK gene involved in the ability to learn. The invention further concerns a method for diagnosing Down's syndrome and mental retardation and an assay therefor, a method for gene therapy of Down's syndrome and a pharmaceutical composition for treatment of Down's syndrome mental retardation.

2. Background Art and Related Disclosures

Down syndrome occurs in about one out of every 800 newborns, with the incidence increasing markedly in the offspring of women over 35. Affecting an estimated one million Americans, it is the leading genetic cause of mental retardation and is associated with a shorter than average life expectancy. Other symptoms are heart and intestinal defects, problems with the immune and endocrine systems, and raft of tissue and skeletal deformities.

Individuals with Down syndrome carry a complete extra copy of chromosome 21 in all of their cells, giving each cell a total of 47 chromosomes rather than the normal 46. For this reason, the condition is also known as "Trisomy 21". There are, however, rare forms of Down syndrome in which only part of chromosome 21 is present in triplicate.

The existence of these rare forms of Down syndrome suggests that the condition may be due to a limited number of genes and led to development of the current invention and to creation of a special series of transgenic mice containing different adjacent segments of human chromosome 21.

Up to date, there is no available treatment of the Down's syndrome mental retardation and learning disability and for correction of this genetic defect.

Recently, with the advent of biotechnology, more and more genetic tools have been developed leading to a new way of treatment of the genetic diseases by gene therapy. To this end, complex trait analysis is assuming increasing importance in understanding mammalian biology. New mapping reagents, such as polymorphic markers distributed throughout the genome described in *Nature*, 380: 152 (1996) and *Prog. Clin. Biol. Res.*, 384:1 (1993), have assisted in the quantitation of the number of genes contributing to such traits and in their localization. Despite these advances, the multi-factorial nature of these traits means that ultimate identification of the responsible genes will be extremely difficult.

Down syndrome can be regarded as a complex trait, as it is likely that numerous genes contribute to the phenotype (*PNAS* (USA), 91:4997 (1994)). The syndrome results in a variety of distinct phenotypes (*PNAS* (USA), 86:5958 (1989) and importantly, is the leading genetic cause of mental retardation in humans, with over 1 million affected in the United States.

Although controversial, there is evidence that an extra dose of one region of chromosome 21 at 21q22.2 may be particularly important in the pathogenesis of the syndrome (ibid). These studies, together with analogous investigations employing mice described in *Nature Genet.*, 11:177 (1995), indicate that the 21q22.2 region, or the region of mouse chromosome 16 syntenic with human chromosome 21, contains genes that affect learning and memory when their dose is increased by a modest amount. These analyses, however, fail to map individual loci contributing to the behavioral abnormalities.

As an approach to fine mapping and identification of loci from 21q22.2 region contributing to learning impairment and behavior observed with Down syndrome when present in an extra dose, the current invention describes multiple lines of transgenic mice containing several contiguous YACs from 21q22.2. This panel of low copy number YAC transgenic is referred to as an in vivo library, because in total a significant segment of about 4% of human chromosome 21 is propagated in vivo, using the mouse as a host and Identifying the genetic material by testing the mouse learning ability and behavior. Using this in vivo library, loci affecting learning and memory from the 21q22.2 region of the human genome could thus be identified in phenotypic screens employing functional assays for behavior.

It is, therefore, a primary objective of this invention to identify loci from chromosome 21q22.2, responsible for Down syndrome, using the Down syndrome as a model for complex trait analysis and utilizing this identification for diagnostic and therapeutic purposes. It is also another objective to determine under which conditions an extra dose of loci from chromosome 21q22.2, when present, contribute to learning abnormalities.

All patents, patent applications and manuscript disclosed in this specification are hereby incorporated by reference.

SUMMARY

One aspect of the current invention concerns a method for prenatal diagnosing and identification of Down syndrome.

Another aspect of the current invention concerns identification of DYRK gene responsible for Down syndrome and involved in the ability to learn.

Still another aspect of the current invention concerns an assay for early prenatal detection of the genetic defect known as Down syndrome and/or mental retardation.

Still yet another aspect of the current invention concerns a gene therapy for corrections of Down syndrome.

Still another aspect of the current invention concerns a generation of transgenic mice bearing a variety of yeast artificial chromosomes gene (YACs).

Still another aspect of the current invention concerns a generation of in vivo library of multiple lines of transgenic mice containing several contiguous YACs from 21q22.2 chromosome.

Still yet another aspect of the current invention concerns primers used for synthesis of complementary DNA of various regions of the DYRK gene.

Still yet another aspect of the current invention concerns primers used for synthesis of complementary DNA of specifically identified locus of chromosome 21 which is responsible for the genetic defect and mutation observed in Down syndrome.

Still yet another aspect of the current invention concerns a cDNA complementary to chromosome 21 locus responsible for Down syndrome.

Still another aspect of the current invention concerns identification of the wild type of chromosome 21 locus corresponding to the locus responsible for Down syndrome and using this wild type DNA to replace the mutated chromosome 21 locus responsible for Down syndrome.

Still yet another aspect of the current invention concerns a method for gene therapy wherein the wild type DNA is delivered into the DYRK gene and replaces the mutated sequence causing Down syndrome.

Still yet another aspect of the current invention concerns radiolabelled probes used for detection of the presence of the complementary sequence by molecular hybridization.

BRIEF DESCRIPTION OF FIGURES

"The file of this patent contains at least one drawing executed in color. Copies of this patent with color drawing (s) will be provided by the Patent and Trademark Office upon request and payment of necessary fee."

FIG. 3 (parts A through D) shows the visible and invisible platform phases of the Morris water maze for YAC transgenic mice containing 152F7 or 152F7 tel or 230E8 and non-transgenic control mice.

DEFINITIONS

Figure 1A:
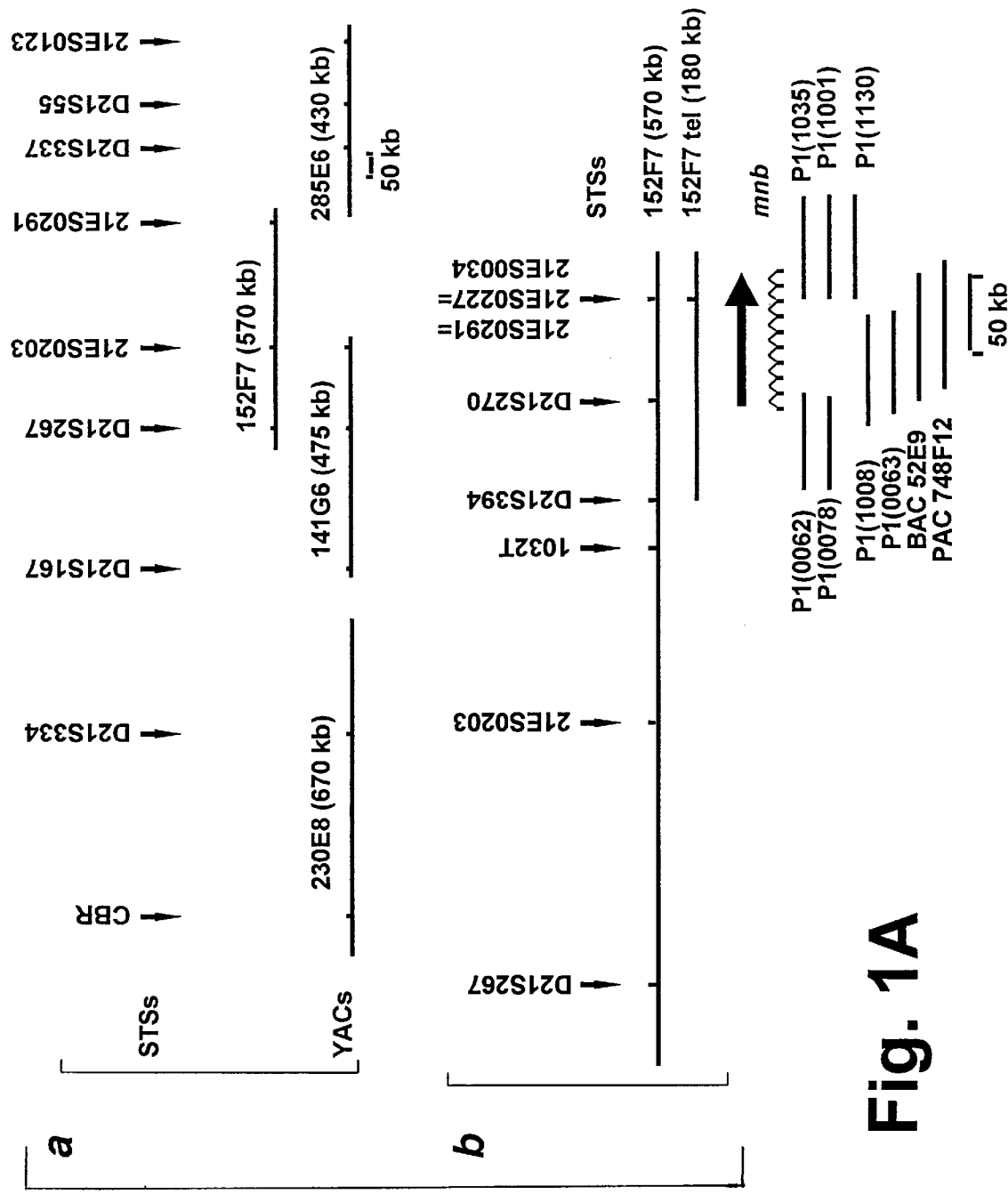
FIG. 1 (parts A and B) shows a molecular map of yeast artificial chromosomes (YACs) used in the creation of transgenic mice (FIG. 1A) and YAC transgene in 152F7 tel mice.

As used herein:

"YACs" means yeast artificial chromosome.

"FISH" means fluorescent in-situ hybridization.

"21g22.2" means chromosome 21g22.2 region or locus of the human genome.

DETAILED DESCRIPTION OF THE INVENTION

This invention concerns identification of a gene involved in learning defects and abnormalities, including such genetic defects as Down syndrome. The invention provides means and tools for development of sensitive diagnostics assay for prenatal detection of Down syndrome and mental retardation and for correction of these defects with gene therapy.

I. Down Syndrome

Down syndrome is a genetic disease associated with autosomal aberrations. In about 95% of cases of Down syndrome, there is an extra chromosome 21.

A. Clinical Symptoms

Typically, the infants, children and adult individuals with Down syndrome are physically and mentally retarded.

The characteristics of the disease are microcephaly, brachycephaly, a flattened occiput slanted eyes, and epicanthal folds. Brushfield's spots (gray to white spots resembling grains of salt around the periphery of the iris) usually are visible in the neonatal period and disappear during the first 12 months of life. The bridge of the nose is flattened, the mouth is often held open because of a large, protruding tongue that is furrowed and lacks the central fissure, and the ears are small with down-folded helixes. The hands are short and broad, with a single palmar crease (simian crease); the fingers are short, with clinodactyl (incurvature) of the $5^{th}$ finger, which often has only 2 phalanges. The feet have a wide gap between the $1^{st}$ and $2^{nd}$ toes, and a plantar furrow extends backward. Hands and feet show characteristic dermal prints (dermatoglyphics). Congenital heart disease is found in about 35% of patients.

The life expectancy of the Down syndrome child is decreased by heart disease and by susceptibility to acute leukemia. Today, most Down syndrome individuals without a major heart defect survive to adulthood, but the aging process seems to be accelerated, with death occurring in the $4^{th}$ or $5^{th}$ decade. At autopsy, all adult Down syndrome brains show the typical microscopic findings of Alzheimer's disease, and many individuals develop the associated clinical signs as well. This suggests a connection between genes on chromosome 21 and Alzheimer's disease, a subject of intense current research.

From the above, it is clear that the Down syndrome possess a serious existential problems for the child, parent and society. It early detection and possibility to correct this genetic defect by gene therapy is, therefore, of utmost importance.

B. Chromosomal Variants

Down syndrome is a genetic disease characterized by distinct genetic features.

Most Down syndrome individual have 47 chromosomes, but some individuals with Down syndrome have 46 chromosomes. These individuals actually have the genetic material of 47 chromosomes except that the additional chromosome 21 has been translocated. Most commonly, the additional chromosome 21 is transferred and attached to a chromosome 14-t(14;21). In about half the cases, both parents will have normal karyotypes, indicating a de novo translocation in the child. Among the remaining couples, one parent (almost always the mother), although phenotypically normal, has only 45 chromosomes, one of which is the t(14;21).

Theoretically, the chance is 1:3 that a mother with a translocation t(14;21) will have a Down syndrome child, but for unknown reasons the actual risk is lower (about 1:10). If the father carries this translocation, the chance is only 1:20, and the reason for this is also not known.

The next most common translocation is (21:22). In this case, the chance that the carrier will have a Down syndrome child is also about 1:10 and the risk for carrier fathers is small. In extremely rare instances, a parent may have a t(21;21). In such a case, 100% of surviving offspring will have Down syndrome.

C. Down Syndrome and an In Vivo Library of 21q22

Down syndrome is the most frequent genetic cause of learning disabilities. Down syndrome is connected with chromosome 21 and seems to have a locus in 21q22.2 region. This region seems to be involved quantitatively because an extra copy of the 21q22.2 region is sufficient to cause the syndrome.

1. Use of In Vivo Libraries for Gene Identification

To identify a specific locus or loci of the 21q22.2 region responsible for the Down syndrome, the thorough investigation of this region was undertaken using multiplicity of transgenic mice carrying a yeast artificial chromosome to generate in vivo library.

The in vivo library approach departs from the traditional strategies and involves making a series of large-insert transgenic animals propagating DNA that covers a particular candidate region of the genome. The region might be chosen based on the presence of a mapped genetic locus that plays a role in a disease or physiological process.

Because of the increased likelihood of including multiple genes as well as large genes, these large-insert vectors (preferably yeast artificial chromosomes, YACs) maximize (multiplex) the amount of information that can be derived from a relatively limited panel of founder transgenic animals. Furthermore, the use of genomic versus cDNA transgenes (because of the presence of normal cis regulatory elements in the former) maximizes the likelihood of obtaining authentic expression patterns and, hence, of obtaining an accurate picture of the true biological function of the genes contained within the transgene. Key features of the in vivo library approach are the absence of a prior assumptions about the identity of genes contributing to the phenotype within the critical region, and careful phenotypic analysis of the different library members to maximize the likelihood of identifying a transgene impacting on the targeted phenotype.

In this case, specifically, an in vivo library of transgenic mice containing 2 Mb of contiguous DNA from human 21q22.2 was created using four overlapping YACs varying between 670 kb and 430 kb. Each member of the library panel contained distinct 430–670 kb overlapping segments of the chromosome 21 region. One, two or several copies of the identified locus were then generated and tested for the impact of the extra genetic information on the learning and memory of the host animals was investigated.

In vivo libraries of this invention were linked with defective learning due to Down syndrome.

2. Use of In Vivo Libraries for Cloning by Complementation

Another successful application of the in vivo library approach for cloning genes based on their function, is classical meiotic mapping and localization of a specific region.

For this purpose, a library of transgenic animals was created that spanned the critical region. To maximize the information derived from each member of the library, each transgenic mouse harbored two distinct but overlapping regions. Reducing the genomic region of interest down to 70 kb, based on functional complementation, dramatically reduced the number of genes requiring investigation. This led to the rapid identification of the mutation responsible for Down syndrome.

3. Linking Gene to Function Using Mice Expressing cDNAs

The gene identified above were further analyzed to decipher their function and a sequence-to-function screening of transgenic mice for a locus responsible for the learning impairment was correlated with a battery of phenotypic assays.

D. Localizing Behavioral Phenotypes in the Library

After the in vivo library was generated, behavioral phenotypes connected with the individual transgenic mice bearing a specific genetic information were correlated with that information.

For this purpose, members of the library were subjected to detailed assays for learning and behavior in order to screen for genes that, when present at an extra dose, affect these phenotypes. From these screens, a 21q22.2 YAC which caused distinct learning and behavioral deficits in several independent lines of mice was identified. The gene on the YAC responsible for the defects was later identified by analyzing animals containing partial fragments of the initial 570 kb YAC. This gene, called minibrain, is of particular interest because when similar mutations of the insect minibrain were found in insects it caused the learning impairment in Drosophila.

The approach employed to identify chromosome 21 genes affecting learning and behavior was based, in part, on the findings that an increased copy number of genes from the 21q22.2 region plays a role in many of the characteristic features of trisomy 21.

One of the YAC transgenes produced distinct learning deficiencies in mice, replicated by two independent lines. These abnormalities seem to be representative of the learning deficits of Down syndrome. Mice containing random fragments of the full-length YAC were used to narrow the critical region for the learning defects from 570 kb to approximately 180 kb.

Large scale sequencing has revealed that the only gene present in the 180 kb interval is the human homolog of the Drosophila minibrain gene. This gene was described to encode a dual specificity tyrosine-serine/threonine kinase expressed in developing neuroblasts and is required for proper learning in Drosophila.

The presence of the human homolog of the minibrain in 180 kb interval supports the current findings that the genetic region connected with learning impairment and the altered dosages of this region causes abnormal neural development and learning deficits in humans as it does in mice nad insect.

II. Identification of Neural Retardation Gene DYRK

A major genetic factor contributing to mental retardation in Down syndrome has now been identified to be present within the DNA region of 21 chromosome.

Such learning deficit have been found to be limited to a gene called DYRK, named after the protein it produces. Any deviation from the normal compliment of two copies of DYRK quantitatively impairs the ability to learn.

The DYRK gene plays an important role in how neuronal pathways are put together and how they function. For development of normal neuronal pathway, two copies of DYRK are needed. When there are more than two copies of DYRK, or when there is only one copy of DYRK gene, learning disability ensues. Thus, where the individual possess altered number of copy of DYRK, or when the DYRK gene expression is altered, the individual suffers from learning disability and mental retardation.

In order to determine the degree of the learning disability and to establish a definite connection between the number of copies of the DYRK gene and the degree of learning disability, transgenic mice carrying segments of human chromosome 21 in their DNA were generated and tested. The below described results clearly show the relationship between the two events. In this context, behavior of the transgenic mice having altered number of copies of DYRK gene led to a discovery of the 21q22.2 locus.

During the process of YAC preparation and microinjection, fragmentation of the lengthy DNA occurs, resulting in fragments which are retained by the fertilized mouse egg in a random fashion. One of the resulting lines of transgenic mice containing fragments of YAC 152F7 (FIG. 1B) was used to localize the gene responsible for learning defects and memory deficits.

To localize this gene in mice containing YAC 152F7, advantage was taken of the observation that fragmentation of the lengthy YAC DNA occurs during handling of microinjection. This led to a panel of animals that contains random fragments of the YAC, in addition to animals containing the full length unrearranged YAC as seen in FIG. 1B. The animals containing random YAC fragments provide a valuable resource for ultrafine structure mapping of genetic traits, since the number of break points obtainable as a result of the fragmentation are far more numerous than one can practicably obtain using classical meiotic genetic mapping. Of the animals containing random fragments of YAC 152F7, animals containing a 180 kb telomeric fragment of the YAC showed learning and memory deficits that were indistinguishable from animals containing the full length YAC, whereas animals containing a complementary 390 kb centromeric fragment showed normal learning and memory. The fragmented YAC studies had thus reduced the interval containing the sequence(s) contributing to the learning defects from 570 to 180 kb. This line of mice (152F tel) contains a telomeric fragment of 152F7 that is approximately 180 kb long, as judged by STS content mapping and FISH. Mice with this telomeric fragment of 152F7 performed nearly identically to mice containing the full length YAC 152F7 on the Morris water maze as seen in FIGS. 3 and 4 and suggests that this region of 152F7 is sufficient to cause the learning defects displayed by full-length transgenic mice.

Consistent with the above findings, mice containing a 390-kb centromeric fragment of 152F7 (152F7 cen) but lacking the 180-kb telomeric region (152F7 tel), were found to perform normally on the Morris water maze (data not shown). This analysis narrowed the critical region of 152F7 responsible for the learning deficits from a 570-kb region (the full length of the YAC) to a 180-kb region (the size of 152F7 tel), as already discussed above.

III. Generation of Transgenic Mice

Transgenic mice carrying various genetic information related to chromosome 21 were generated and behaviorally tested. These mice were particularly designed for testing of human chromosome 21 in connection with Down syndrome.

Transgenic mice carrying chromosome 21 for detection, testing and functional screening of human chromosome 21q22.2 region were generated according to Examples 1 and 2.

A. Transgenic Mice

Transgenic mice, containing four different yeast artificial chromosomes (YACs) that together cover approximately 2 megabases (Mb) of contiguous DNA from 21q22.2 were generated. Independent lines derived from each of these YAC transgenes were subjected to a series of behavioral and learning assays.

Two of the four YACs which caused defects in learning and memory in the transgenic animals were identified and distinguished from the other two YACs which had no effect. The most severe defects were found to be caused by a 570-kb YAC and the interval responsible for these defects was narrowed to a 180-kb critical region as a consequence of YAC fragmentation.

This region was further found to contain the human homologue of a Drosophila gene, minibrain, and therefore, strongly implicates this region in learning defects associated with Down syndrome.

Figure 1B:
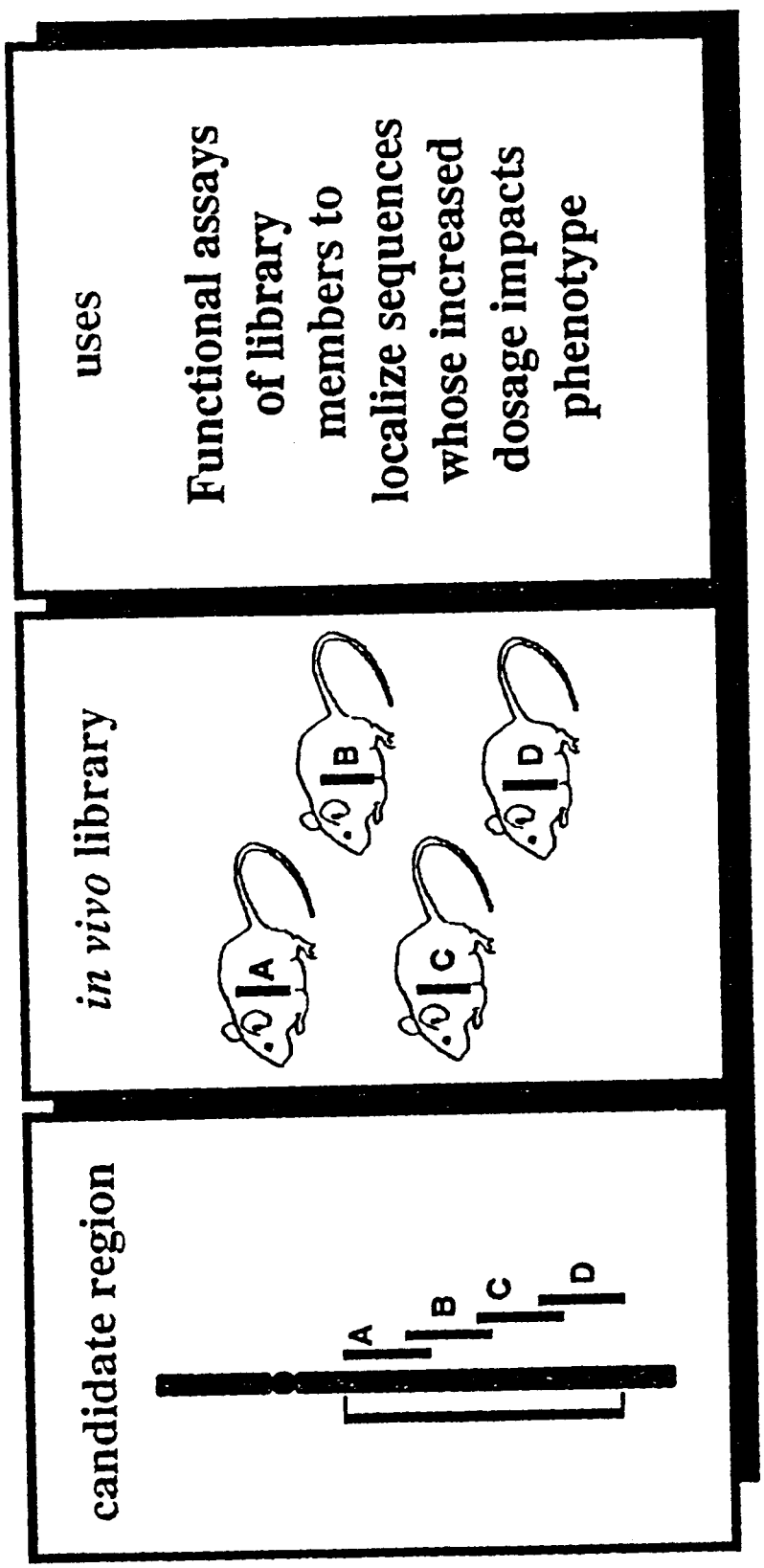

Molecular map of yeast artificial chromosomes (YACs) used in the generation of panel of transgenic mice and copy number and integrity of the YAC transgene is seen in FIGS. 1A and 1B and in FIGS. 2A–2J.

The YACs from 21q22.2 used to create the transgenic animals are diagrammed in FIG. 2A. FIG. 1A shows molecular map of the YACs from 21q22.2 used to create the panel of transgenic mice. FIG. 1B illustrates the event of the YAC transgene in 152F7 tel mice as judged by STS content mapping. The human minibrain gene and its direction of transcription is also shown.

The intron/exon structure of the human minibrain gene is highly conserved, though the intron sizes in the human gene are unknown. Mapping has accurately placed the 5' and 3' ends of the gene, and the intervening exons were evenly spaced for diagrammatic purposes. The large insert clone map in the region of the minibrain gene is also shown. Even the largest of the clones fails to entirely encompass the gene.

Figure 2:
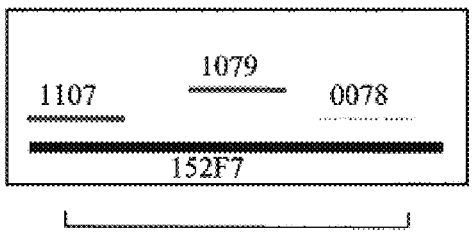
FIG. 2 (parts A through J) shows analysis of YAC transgenic mice using multi-color fluorescence in situ hybridization.
Figure 2:
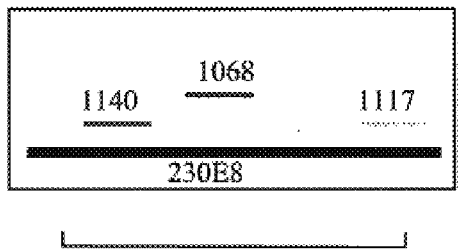
Figure 2:
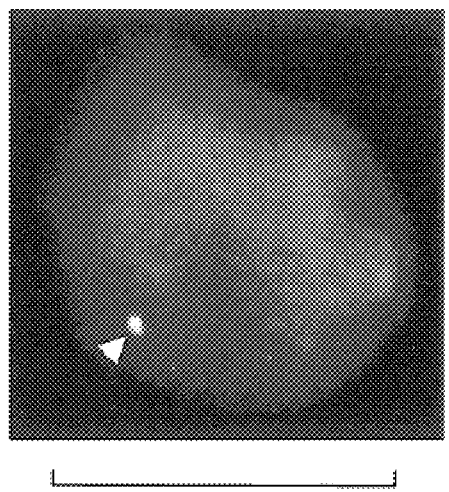
Figure 2:
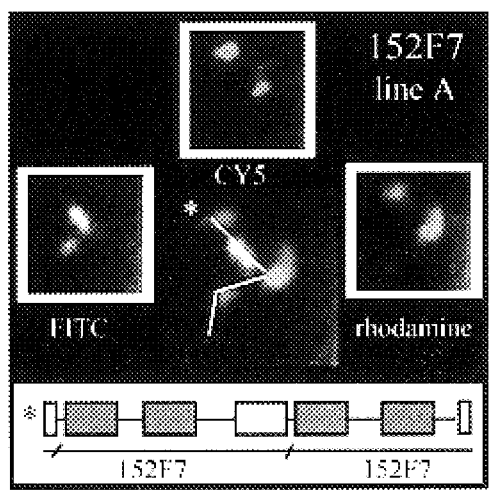
Figure 2:
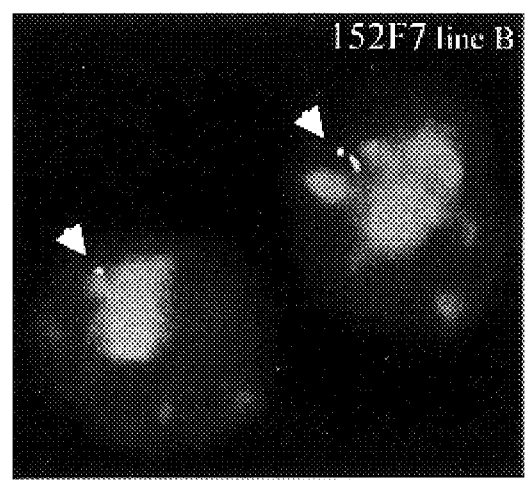

FIG. 2 shows analysis of YAC transgenic mice using multi-colour fluorescence in situ hybridization. FIGS. 2A and 2B are the diagrams showing the relative positions of P1 (top) and YAC DNA probes (bottom) and the colour scheme. Probes shown in blue, green and red were detected in the infrared (CY5), green (FITC) and red (rhodamine) wavelength intervals, respectively. The maps are depicted with the centromere to the left, and the telomere to the right. The conclusions from the FISH analysis assume the shortest chromatin path distance.

FIG. 2C shows a mononuclear white blood cell (WBC) (5,800×) from 152F7 tel displaying overlapping signals for P1 probes 1079 and 0078 (arrowhead). The hybridization domain appears yellow due to the overlap of red and green fluorescence and the results indicate one copy of the telomeric fragment in the transgenic mice.

FIG. 2D shows analysis of cells from 152F7 line A indicated the presence of the copies of the YAC. The panel shows the individual images from FITC, CY5 and rhodamine-labelled probes (all ×4,100). Only the part of the cell containing the hybridization domains is shown. The composite colour picture in the center (×5,800) shows the FITC, CY5 and rhodamine-labelled probes in green, blue and red, respectively. A white line connects the hybridization domains. The schematic at the bottom indicates a possible arrangement of the transgene, beginning at one CY5/rhodamine hybridization domain (●) and following the white line. Alternate arrangements could be possible, for example when the two copies of the YAC would be arranged in a head-to-head array in the opposite orientation to each other. However, the FIG. 2D scheme depicts the simplest explanation. The presence of more than two copies of the telomeric section of the YAC is suggested by three red hybridization signals.

FIG. 2E shows that 152F7 line B transgenic mice contained one copy of the YAC and hybridization of the P1 probes showed one signal for each of the probes. The panel shows two interphase cells (3,400×) counterstained with DAP1 (blue). The arrowheads point to hybridization signal domains corresponding to P1 probes 1079 (green) and 0078 (red). In each of the cells, one hybridization signal corresponding to hybridization by P1 probe 1107 was found in the vicinity of the signals presented (data not shown).

FIGS. 2F–2I analysis of YAC 230E8 line A transgenic mice demonstrated two copies of the YAC. P1 probes were labelled as shown in FIG. 2B.

As seen in FIG. 2E, two hybridization signals were observed for each of the probes. The panels show images (×3,200) recorded in individual wavelength intervals (FIG.

2F: green, FIG. 2G: red, FIG. 2H: infrared) and a colour composite seen in FIG. 2I. In FIG. 2I, the DAPI counterstain is shown in gray. Overlap between hybridization domains lead to mixed colours seen in FIG. 2I.

FIG. 2J shows 230E8 line B mice that contained a complete single copy of the YAC as suggested by the presence of all three hybridization signals from P1 clones 1140, 1068 and 1117. The panel (×5,800) shows the DAPI counterstain (blue) and hybridization signals from probes 1068 (green) and 1117 (red).

Together, the transgenic animals contained approximately 2 Mb of DNA from 21q22.2. Three colour fluorescent in Situ hybridization (FISH) was employed to assess the copy number and integrity of the YAC transgenes 152F7 and 230E8, as illustrated in FIGS. 2A–J. The copy number of 1–3 inserts of each of the YACs was consistent with results obtained from Southern blotting and quantitative PCR (*Genomics*, 27:425 (1995).

B. Behavioral Testing

Transgenic mice generated above were submitted to behavior testing. Methods for behavioral testing of transgenic mice generated as described above are described in Examples 3–5.

Upon initial handling as described in Example 3, mice containing YAC 152F7 (both lines A and B, and 152F7 tel) reacted similarly to non-transgenic mice, but became increasingly more agitated as handling continued. Unlike non-transgenic mice which splayed out all four limbs, these transgenic mice showed a tendency to curl into a ball when held by the tail. This tendency is a non-specific indication of neurological defects (*Cell*, 75:1263(1993)). The other YAC transgenic mice could not be distinguished from non-transgenic controls.

The transgenic and non-transgenic animals with the FVB background performed very poorly on the Morris maze because of the recessive retinal degeneration. To circumvent this, transgenic/FVB males were mated with C57/BL6 females to produce F1 hybrid males which were employed for all the behavior testing. Barring possible epigenetic effects (such as imprinting) due to the FVB or C57/BL6 alleles being from either the male or female grandparent, the F1 hybrids are genetically identical except for the presence or absence of the transgene.

In the Morris water maze described in Example 4, the mice learn the position of a platform submerged under water in a swimming pool by relating it to objects in the room. After these learning trials, the platform is removed from the pool and the swimming of the mice analyzed for a 1 minute period. This probe test assesses the learning of the mice by quantitating the persistence with which they search the vicinity of the swimming pool where the platform had been located. The transgenic mice containing 152F7 and 230E8 and the non-transgenic control mice spent an equal amount of time exploring the quadrant of the pool where the platform had been formerly located as seen in FIG. 3.

When tested in Morris water maze according to Example 4, YAC transgenic mice containing 152F7, 152F7 tel or 230E8 and non-transgenic control mice shows the visible and invisible platform phases as seen in FIG. 3.

FIG. 3A shows the visible platform test where all groups of animals showed significant improvement over trials (F[5,954]=143.24, P<0.0001). There were no significant differences between YAC transgenic mice containing 152F7 or 230E8 and non-transgenic control mice. 152F7 tel mice were slower than non-transgenic mice (F[1,414]=16.41, P<0.0001), but nevertheless showed significant improvement over trials (F[5,138]=21.17, P<0.0001).

FIG. 3B shows the invisible platform test. 152F7 line A was not significantly different from non-transgenic animals (F[1,558]=0.25, P=0.61) but line B was significantly slower (F[1,558]=12.33, P=0.0005). 230E8 line A was not significantly different from non-transgenic animal (F[1,630]=0.63, P=0.43), but line B was significantly slower (F[1,558]=7.69, P=0.0058). The graph shows the performance of 152F7 line B and 230E8 line B. There was no significant difference between 152F7 tel mice and non-transgenic mice. The 152F7 tel mice also showed no difference with the two lines of full-length 152F7 mice. All groups of animals showed significant improvements over trials (F[8,1323]=18.04, P<0.0001.

FIG. 3C shows the probe test (dwell). The percentage time spent in each of the four quadrants of the pool was analyzed. Using Dunnett's post-hoc comparison, no significant differences were found between the performance of the YAC transgenic mice and the non-transgenic mice as judged by comparing the amount of time spent in the quadrant of the pool where the platform had been situated.

FIG. 3D shows the probe test (platform crossings). The number of times the mice crossed an imaginary platform in each of the four quadrants of the pool was analyzed. On this measure of performance, both 152F7 full-length (P<0.00031m Dunnett's post-hoc comparison) and 152F7 tel (P<0.00051 Dunnett's post-hoc comparison) YAC transgenic mice performed significantly more poorly than non-transgenic mice as judged by comparing the number of times the animals crossed the position where the platform had been located. The performance of the 152F7 tel mice was indistinguishable from the full length 152F7 transgenic mice (P>0.64, t-test, two tailed).

As seen in FIG. 3, both lines of mice containing YAC 152F7, however, crossed significantly less frequently over the site of the original platform than the other YAC transgenic mice and non-transgenic mice. The deficits shown by the 152F7 YAC transgenic mice are similar to those shown by mice lacking PKCY as described in *Cell*, 75:1263 (1993).

The reverse platform test was used for additional learning deficits testing. In this task, the mice were required to learn a novel position for the invisible platform which was placed in the quadrant opposite to its initial location.

When the learning deficits of the transgenic mice of the invention were investigated suing the reverse platform test, it was found that the YAC 152F7 mice were significantly slower in learning than their tested counterparts. Results are seen in FIG. 4.

FIG. 4 illustrates learning deficit testing using the reverse platform phase of the Morris water maze.

Figure 4A:
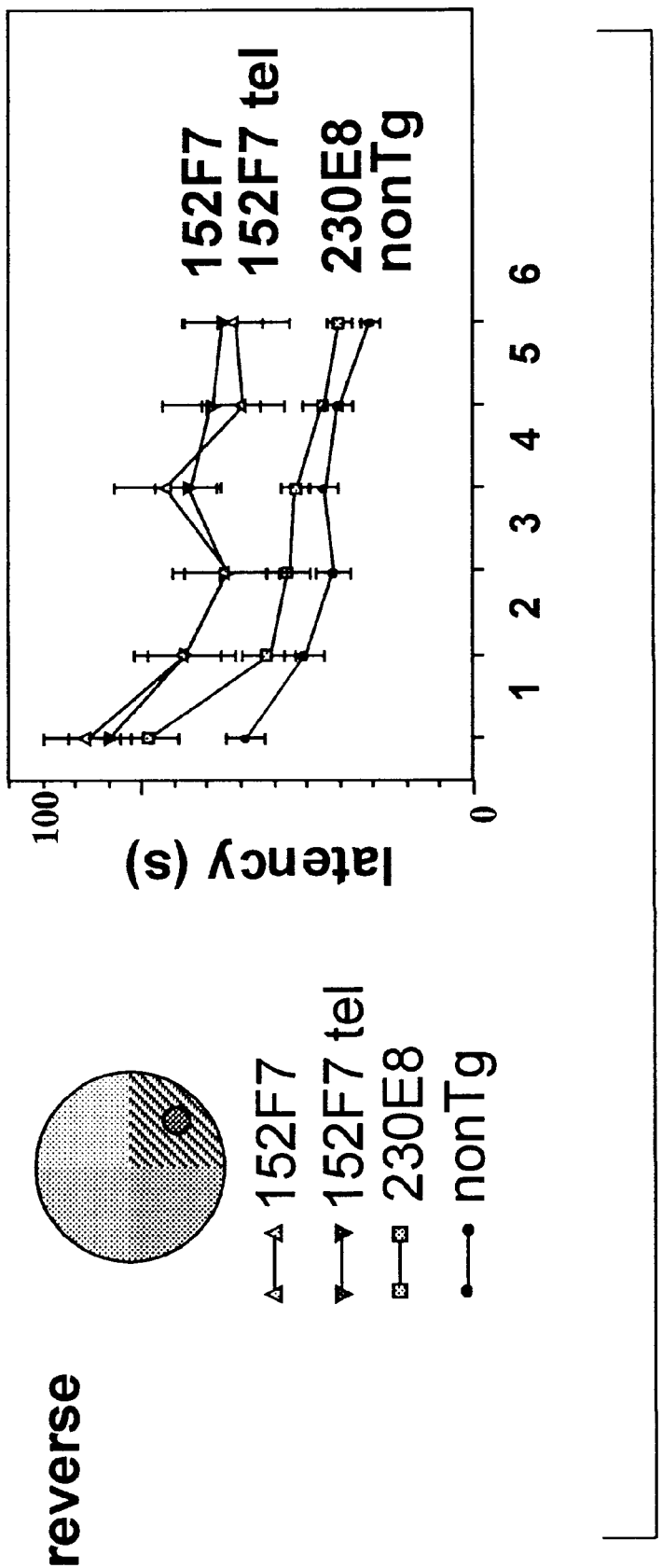
FIG. 4 (parts A through C) shows the reverse platform phase of the Morris water maze, (FIG. 4A); reverse probe (dwell) (FIG. 4B) and reverse probe (crossing), FIG. 4C.

FIG. 4A shows that 152F7 transgenic mice did not show any significant learning of this task (F[5,1381]=1.12, P=0.36) and their performance was comparable to mice containing the full length YAC. Both 230E8 YAC transgenic mice and non-transgenic mice (F[5,534]=16.82, P<0.0001) showed significant evidence of learning. However, the 230E8 mice were slower at acquiring the task than non-transgenic mice (F[1,534]=13.44, P=0.0003.)

As seen in FIG. 4A, both lines of mice containing YAC 152F7 failed to show significant decreases in latency, whereas both lines of mice containing YAC 230E8 showed significant decreases, but were less effective than mice containing either YAC 141G6 (data not shown) or 285E6 (data not shown) or the non-transgenic mice, all of which efficiently learned the new platform position.

FIG. 4B shows reverse probe (dwell). Both 152F7 mice (P<0.0013, Dunnett's post-hoc comparison) and 152F7 tel mice (P<0.012, Dunnett's post-hoc comparison) fared significantly more poorly than the non-transgenic controls, spending less time than non-transgenic mice exploring the quadrant of the pool where the reversed platform had been situated. The performance of the 152F7 tel mice was indistinguishable from the full length transgenic mice (P>0.87, t-test, two tailed).

FIG. 4C shows reverse probe (crossings). The 152F7 mice (P<0.0001, Dunnett's post-hoc comparison), the 152F7 tel mice (p<0.0001, Dunnett's post-hoc comparison), and the 230E8 mice (P<0,0017, Dunnett's post-hoc comparison) performed significantly less effectively than non-transgenic mice on this test, as judged by comparing the number of times the animals crossed the position where the reversed platform had been located. The performance of the 152F7 tel mice was indistinguishable from the full length 152F7 transgenic mice (P>0.26, t-test, two tailed).

In the reverse probe test, in all tested conditions, as seen in FIGS. 4A–4C, mice containing YAC 152F7 also performed much worse than two other transgenic mice containing either YAC 141G6 (data not shown) or 285E6 (data not shown) or the non-transgenic mice, spending substantially less time in the quadrant of the pool where the reversed platform had been located and crossing the position of the platform much less frequently. Mice containing YAC 230E8 spent the same amount of time as mice containing either YAC 141G6 (data not shown) or 285E6 (data not shown) or the non-transgenic mice in the quadrant of the pool where the reversed platform had been located, but the 230E8 transgenic mice crossed the position of the platform much less frequently.

These findings demonstrate that the extra genetic information contained in YACs 152F7 or 152F7 tel causes distinct spatial learning and memory deficits compared to mice containing YACs 141G6 or 285E6 or the non-transgenic control mice. Importantly, for each YAC, similar results were obtained from two independent lines of transgenic animals.

C. Histopathology

To investigate possible neuropathological correlates of the learning and memory defects, the YAC transgenic mice at approximately one year of age were examined for the presence of gross anatomical and microscopic abnormalities. Methods are described in Example 6. Results are seen in FIG. 5.

FIG. 5 are neurohistopathology results of the YAC transgenic mice.

Specifically, FIG. 5A shows staining of the cerebral cortex at the level of the caudate nucleus with GFAP antibodies. The photomicrograph (×25) shows the sections from 230E8 (left) and 152F7 (right) animals. Numerous astrocytes can be seen in the white matter to the right of the section (indicated by the arrows), but none are visible in the cortex at the left.

FIG. 5B shows a staining of the cerebral cortex at the level of the caudate nucleus with Luxol fast blue and cresyl violet (LFB-CV). The photomicrograph (×10) shows the sections from 230E8 (left) and 152F7 (right) animals. The cortex can be seen at the top of the photomicrograph, and the myelin of the corpus callosum, fornix and internal capsule can be seen stained blue.

FIG. 5C is higher power (×25) view of the cortex from the sections shown in FIG. 5B (230E8 left, 152F7 right). The cortex is at the top of the photomicrograph and the white matter is at the bottom.

Figure 5D:
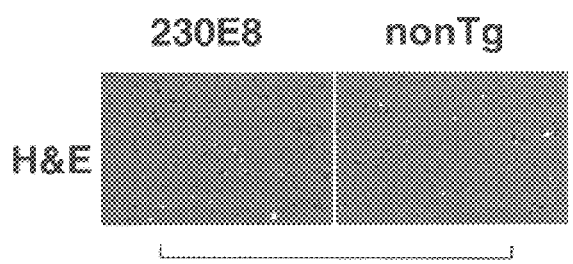
FIG. 5 (parts A through E) shows results of neurohistopathological studies of the YAC transgenic mice, staining of the level of the caudate nucleus with GFAP antibodies, (FIG. 5A); with luxol fast blue (FIG. 5B); higher power view of the cortex from the FIG. 5B section (FIG. 5C); hematoxylin and easier and neuronal densities of the cerebral cortex of the level of the caudate nucleus.

FIG. 5D shows a staining of the cerebral cortex at the level of the caudate nucleus with hematoxylin and eosin (H&E) (meninges up, white matter down). The photomicrograph (×100) shows the sections from 230E8 (left) and non-transgenic (right) animals.

Figure 5E:
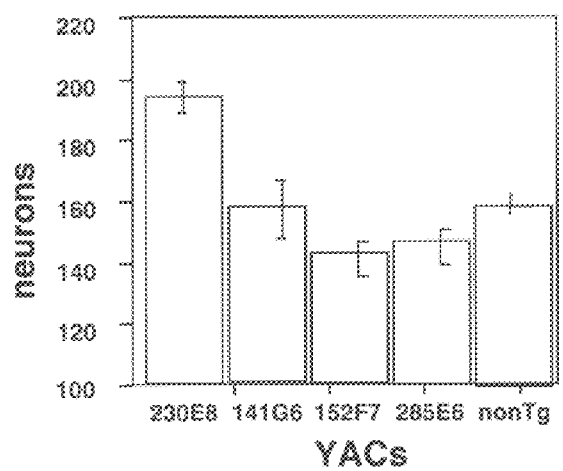

FIG. 5E shows neuronal densities in the cerebral cortex at the level of the caudate nucleus. The ordinate shows the number of neurons per ×50 field. Mice containing YAC 230E8 showed significantly greater neuronal densities than non-transgenic mice (P<0.015, Dunnett's post-hoc comparison).

In this study, all major organs were inspected, including the prominent systems involved in Down syndrome, the brain, heart and gut. Aside from the brain and eyes, no defects were detected in the transgenic mice, apart from what would be expected for normal aging. Retinal degeneration seen in the transgenic and non-transgenic mice is almost certainly due to a recessive mutation in the locus Pdeb. This mutation is present in the FVB strain used for creation of the transgenic.

Immunohistochemical analysis of brains using antibodies to glial fibrillar acid protein (GFAP) were used to detect reactive gliosis, as seen in FIG. 5A, a condition where astrocytic glial cells display hypertrophy with enlarged, elongated processes in response to neuronal loss. Astrogliosis was found in the white matter of all mice. This degree of astrocytosis is not normal in mice of comparable age from most strains, but is known to occur in FVB mice. Staining of brains with either Luxol fast blue-cresyl violet (LFB-CV) for myelin seen in FIGS. 5B and 5C, or hematoxylin and eosin (H&B), seen in FIG. 5D, did not reveal any abnormalities in neurons or glia.

To assess neuronal densities in the cerebral cortices of the mice, neurons in the microscopic fields of H&E stained sections were counted as seen in FIG. 5E. Mice containing YAC 230E8 displayed significantly greater cortical neuronal density than the other YAC transgenic mice or non-transgenic controls (P<0.015, Dunnett's post-hoc comparison). The abnormal cortical neuronal density of the 230E8 mice may play a role in their learning abilities. The lowest neuronal density of 157F7 mice tends to support their inability to learn seen in testings shown in FIGS. 4 and 5.

D. Electrophysiological Analysis

Long-term potentiation (LTP) is an important cellular mechanism underlying learning and memory and is a prominent feature of excitatory synaptic transmission in the hippocampus. This region of the brain is essential for certain forms of learning and memory and for normal performance of the Morris water maze. Electrophysiological testing was performed according to Example 7.

The 152F7 YAC transgenic mice showed the most severe defects on this test and their deficits were similar to those of PKCY knockout mice which have abnormalities in LTP20. Therefore, the spatial learning defect in the 152F7 animals was investigated for its association with abnormal hippocampal LTP. The amount of LTP induced in slices from the 152F7 animals using a conventional high frequency (100 Hz) stimulation protocol was indistinguishable from that seen in slices from non-transgenic animals. Results are illustrated in FIG. 6.

Figure 6A:
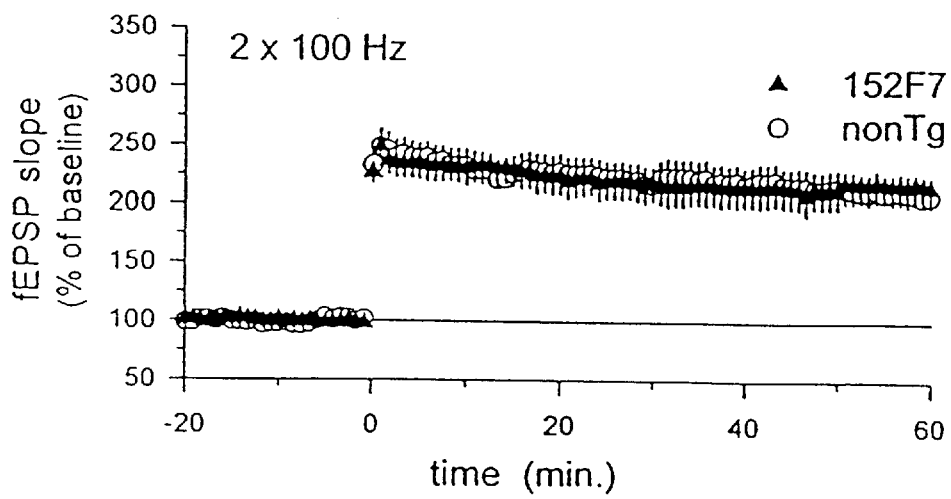
FIG. 6 (parts A through C) shows hippocampal long term potentiation and paired-pulse facilitation in 152F7 transgenic mice, sixty minutes after inducing LTP with high frequency stimulation (FIG. 6A); low frequency stimulation-induced LTP (FIG. 6B) and paired-pulse facilitation in hippocampal slices from 152F7 mice (FIG. 6C).

FIG. 6A illustrates hippocampal long term potentiation and paired-pulse facilitation in 152F7 transgenic mice and nontransgenic mice. As seen in FIG. 6A which is a graph showing results obtained sixty minutes after inducing LTP with high frequency stimulation (2×100 Hz, delivered at time=0) {EPSTPs in slices from 152F7 mice were potentiated to 213.7±15.3% of baseline (mean±SEM, n=10 animals, 15 slices), such long-term potentiation was normal in 152F7 transgenic mice.

Because the presence of apparently normal LTP in animals with learning deficits in the Morris water maze was found, examination was undertaken to determine whether low frequency stimulation-induced LTP was abnormal in the 152F7 mice. Similar levels of LTP following a 30 second train of low frequency (5 Hz) stimulation in slices from 152F7 and control animals were observed as seen in FIG. 6B.

Figure 6B:
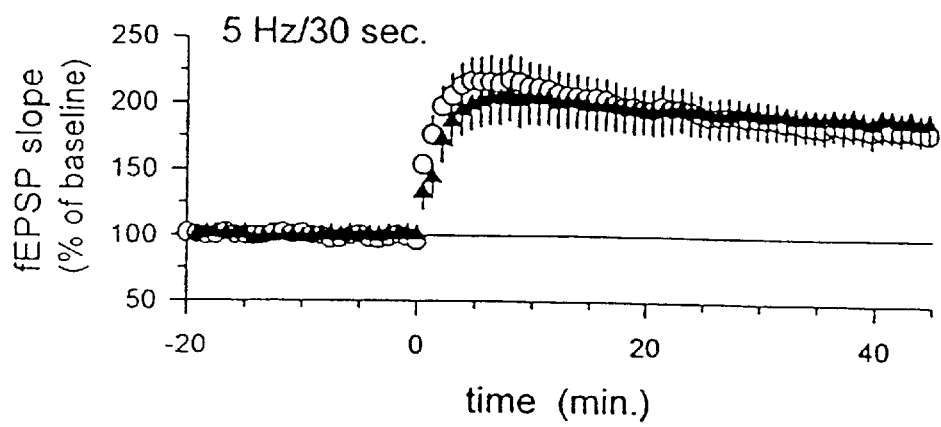

FIG. 6B shows results obtained following low frequency stimulation-induced LTP in the 152F7 mice and nontransgenic mice. As seen in FIG. 6B, 45 minutes after a 30-s long train of 5 Hz stimulation (delivered at time=0) fEOPSPs in slices from 152F7 mice were potentiated to 187.8±16.4% of baseline (n=12 animals, 14 slices) the low frequency stimulation-induced LTP was also normal in 152F7 transgenic mice.

Figure 6C:
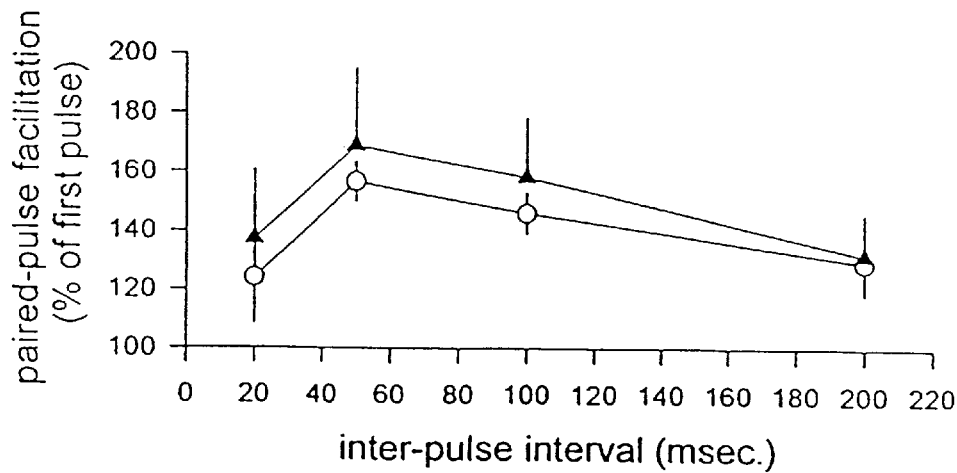

Furthermore, paired-pulse facilitation, a short lasting form of synaptic plasticity that is seen when pre-synaptic fibers are activated with pairs of stimulation pulses delivered at short time intervals, was similar in 152F and non-transgenic mice, as seen in FIG. 6C.

FIG. 6C shows results of paired-pulse facilitation in hippocampal slices from 152F7 mice (n=5 animals, 3 from line A and 2 from line B, total number of slices n=9) and non-transgenic control animals (n=6 animals, 13 slices).

E. Locomotor Activity

The locomotor activity and control over the locomotor activity is an excellent measure of coordination and is therefore useful for determination of the neural defects. The locomotor activity of 152F7, 152F7 tel and non-transgenic animals was assayed over a one hour period, according to Example 5. Results as seen in FIG. 7.

Figure 7:
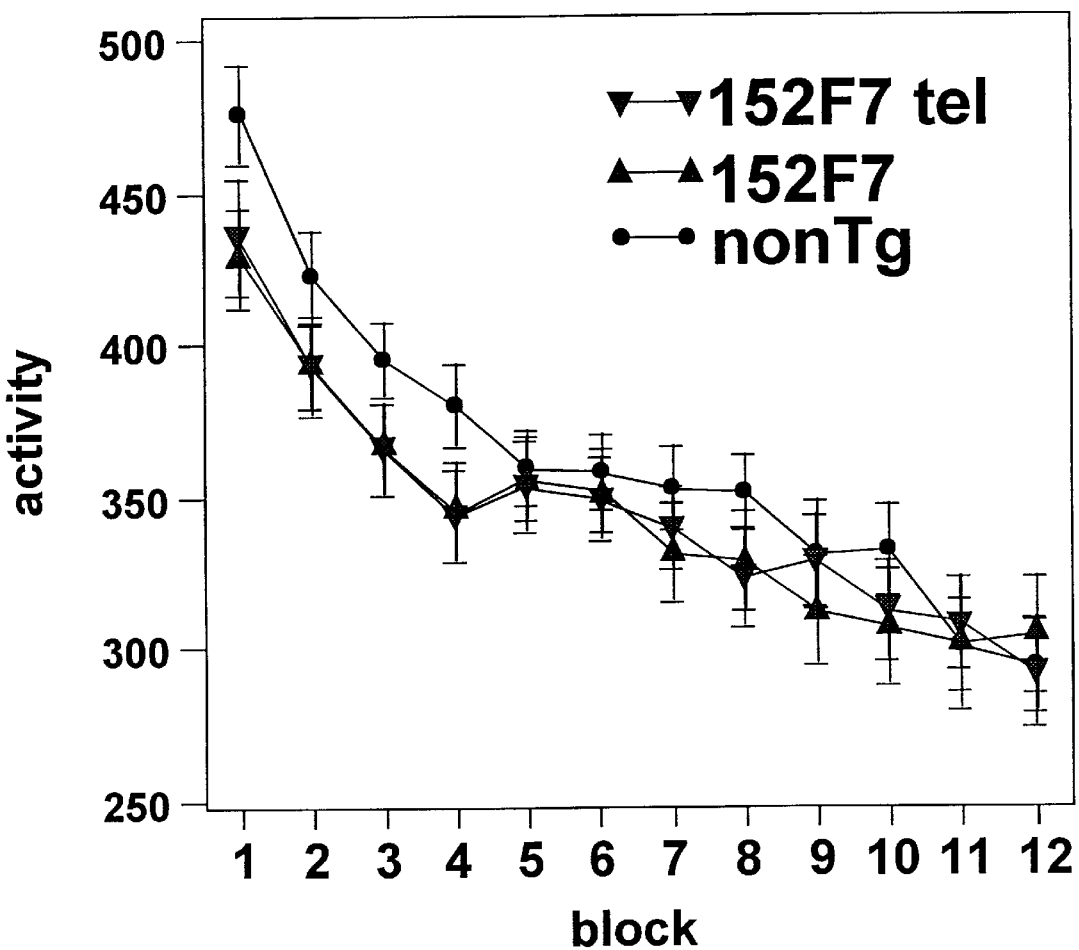
FIG. 7 shows activity of full-length 152F7 YAC transgenic mice.

FIG. 7 illustrates the activity of full-length 152F7 YAC transgenic mice (line A), 152F7 tel YAC transgenic mice and non-transgenic controls. The activity of the mice was measured over a one hour period, split into 12 blocks of 5 minutes each. All groups tested showed significant habituation (F[11, 1260]=26.52, P<0.0001) over the 1-hour period. Both lines of 152F7 showed significant hypoactivity (line A: F[1, 780]=7.32, P=0.007; line B: F[1, 720]=47.31, P<0.0001), as did 152F7 tel (F[1, 792]=6.59, P=0.010. The graph shows the results for 152F7 line A, 152F7 tel and non-transgenic mice.

As seen in FIG. 7, all the groups of animals showed significant habitation, with the activity decreasing significantly over the period of testing. However, mice containing either 152F7 or 152F7 tel displayed locomotor hypoactivity compared to non-transgenic controls in almost all phases of testing. Thus, the region of 152F7 responsible for the learning defects of the transgenic mice is also the same as the region responsible for the locomotor hypoactivity.

IV. Human Minibrain

Human minibrain, because of its similarity to the homologous regions controlling learning behavior in insect and mice, was a good candidate gene for the learning arid locomotor defects shown by 152F7 transgenic mice.

The human homolog of the Drosophila minibrain gene was described in *Hum. Mol. Genet.*, 5:1305 (1996). The human homolog is over 100 kb long, as shown by mapping to a dense large insert (P1/PAC/BAC) contig in the region and is not encompassed by any clones from the contig, but is however, completely contained in the telomeric fragment of 152F7 (152F7 tel). The product of this gene was found to be a dual specificity tyrosine/serine-threonine kinase expressed in developing neuroblasts.

This gene could, therefore, be an attractive candidate for the learning and locomotor defects seen in the 152F7 mice.

To confirm this expectation, RT-PCR was used to demonstrate expression of the human minibrain gene in the 152F7 and 152F7 tel YAC transgenic mice. Results are seen in FIG. 8.

Figure 8A:
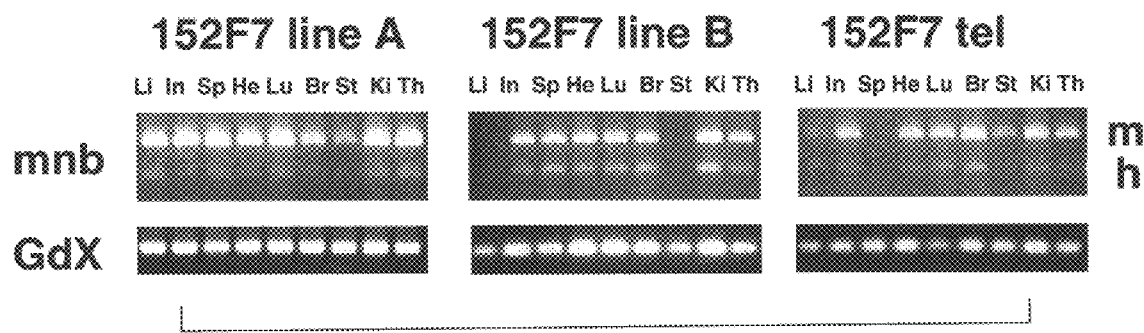
FIG. 8 (parts A through C) shows expression of the human minibrain gene in the 152F7 and 152F7 tel YAC transgenic mice; RT-PCR (FIG. 8A); quantitation of human minibrain expression in the YAC transgenic mice (FIG. 8B) and the histogram of total minibrain transcripts in the transgenic mice (FIG. 8C).

FIG. 8A is RT-PCR performed according to Example 1, using primers described therein. FIG. 8A shows that the mouse minibrain gene is widely expressed and that the human minibrain transgene expression mirrors the expression of the endogenous mouse gene. In FIG. 8A, mouse and human minibrain transcripts are indicated by "m" and "h" respectively. The investigated tissues were liver (Li), intestine (In), spleen (Sp), heart (He), lung (Lu), brain (Br), stomach (St), kidney (Ki), and thymus (Th). Equal loading is shown by the expression of GdX, a housekeeping gene. Similar results were obtained using primers recognizing the housekeeping gene G3PDH (data not shown).

The absence of detectable endogenous and transgene transcript from the liver and stomach of 152F7 line B and the spleen of 152F7 tel is due to loss of the RNA, which is consistent with the decreased signal from the positive control GdX primers in these lanes. For all the experiments shown in the FIG. 8A, absence of contaminating genomic DNA from the RNA preparations was confirmed based on two findings that all three sets of primers, that is minibrain primers, GdX primers and G3PDH primers, gave no detectable signal from a mock RT-PCR reaction in which reverse transcriptase had been omitted, that the GdX primers span an intron and hence give different-size PCR products from genomic DNA and cDNA and that no genomic product was detected.

Figure 8B:
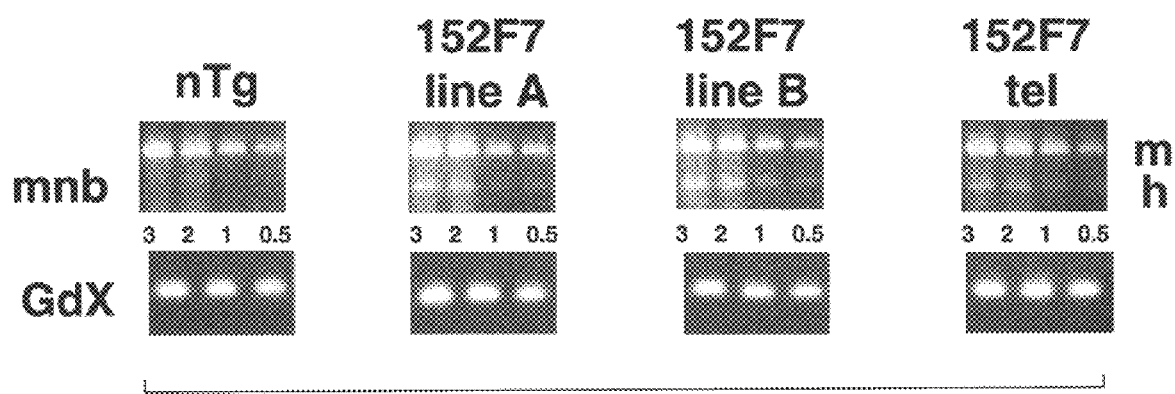
Figure 8:
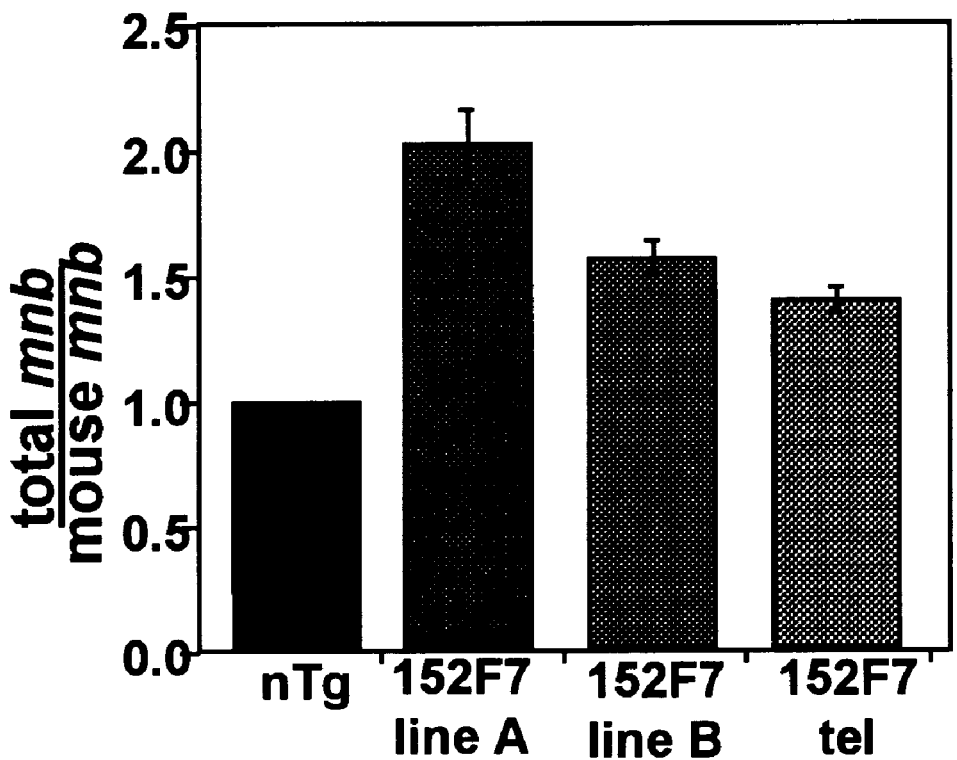

FIG. 8B shows quantitation of human minibrain expression in the YAC transgenic mice. Varying amounts of brain cDNA from transgenic and non-transgenic (nTg) mice were used in PCR reactions in a range where a linear response of PCR product was obtained. The relative volume ($\mu$l) of reverse transcription reaction used in each PCR reaction is shown below the corresponding lane.

FIG. 8C is a histogram showing the ratio of total minibrain transcripts in the transgenic lines compared to the level of minibrain transcript in non-transgenic controls. Normalization between the cDNA samples to control for different loadings was employed using the GdX signal, which was in the linear range. FIG. 8C shows results from measurement of six separate reactions for each transgenic line and the non-transgenic controls. Standard error bars are shown for the transgenic mice. As the non-transgenic mice, by definition, have a ratio of one, these animals are depicted for reference and no error bars are shown.

As seen in FIG. 8C, using Dunnett's post-hoc comparison, the transgenic lines 152F7 seen in line A (P<<0.0001), 152F7 seen in line B (P<0.0005) and 152F7 tel (P<0.012), possessed significantly higher total levels of minibrain transcripts than the non-transgenic controls nTg.

As seen in FIG. 8A, the gene was widely expressed, including in the brain. Moreover, the human transgene was expressed in a profile that closely mirrored the expression of the endogenous mouse gene. Furthermore, the human minibrain gene was expressed in the 152F7 tel mice in a profile very similar to that of the full length YAC transgenic mice.

Quantitative RT-PCR was used to estimate the level of expression of the human minibrain transgene as seen in FIGS. 8B and 8C. Within the limited quantitative capabilities of this technique, the transgenes appeared to cause low level expression, comparable to the endogenous genes. The 152F7 line A mice had about twice the level of minibrain transcripts compared to non-transgenic controls and 152F7 line B and 152F7 tel mice had about 50% more message than controls. This is consistent with the relative copy numbers of the transgenes in these lines of mice as seen in FIG. 2.

Results described above of analysis of human 21q22.2 in transgenic mice show that YACs 152F7 and 230E8, as low copy number transgenes, caused specific but differing defects in learning and memory. The distinct behavioral phenotypes caused by these two YACs is consistent with findings in humans demonstrating that imbalance of more than one region of chromosome 21 can affect behavior and suggests that there is more than one locus in 21q22.2 that can have an impact on learning.

Confirmation of the above results from the additional testing of transgenic mice containing YACs 141G6 and 285E6. These mice performed normally during the the Morris water maze testing. This shows that the learning defects shown by the 152F7 and 230E8 YAC transgenic mice were specifically caused by expression of human genes contained within these YACs, and was not due to non-specific defects resulting from transgenesis with large segments of DNA. Significantly, in all cases similar phenotypes were shown by two independent lines of mice containing the same YAC, indicating that the observed phenotypes are not due to insertion effects. Differences in the severity of the phenotype between separate lines of the same YAC seems to be related to copy number as seen in FIG. 2 and expression of the transgenes, as seen in FIG. 8.

Of the, two YACs that caused learning defects, a neuropathological correlate was found in animals containing one of the YACs. 230E8 YAC transgenic mice had a significantly increased neuronal density in the cerebral cortex compared to non-transgenic controls. The abnormal cortical neuronal density of the 230E8 mice seems to play an important etiological role in their deficits in the learning and memory tests. Previously, as described in *Neurology*, 45: 1581 (1995), increased neuronal density has been linked with learning deficits and cognitive abnormalities and may cause these defects by interfering with neuronal signalling. However, just to the contrary, Down syndrome was associated with decreased neuronal numbers (*Nature*, 378: 776 (1995)), which corresponds to findings seen in FIG. 5E, showing that YAC 152F7 transgenic mice have significantly lower number of neurons compared to nontransgenic mice.

The invention describes transgenic mice engineered to have increased dosage of large but defined regions of genome containing DYRK distinct loci on chromosome 21 which affect learning and behavior, and identified a candidate gene responsible for defects seen in the 152F7 YAC transgenic mice.

V. Effect of Human 21q22.2 Sequences on Learning in Mice

Analysis of the transgenic mice described above, has revealed that one 570 kb YAC, in two separate founder lines, was associated with distinct learning deficits compared with the other 21q22 YAC transgenic and non-transgenic control animals. We have localized the gene on the YAC that causes the deficits by taking advantage of fragmentation of the YAC during the process of microinjection. The responsible gene is the human minibrain gene, and the homolog of the gene in Drosophila is also associated with learning defects. These results show that altered dosage of minibrain is associated with abnormal neural development in flies and mice and, in humans, may also be involved in the molecular pathology of Down syndrome.

VI. Effect of Increased Dose of 21q22.2 on Defined Phenotypes

Results presented above show that irregularities in gene expression and particularly the multiple number of copies cause the learning disabilities.

Evidence shows that an extra copy of the 21q22.2 segment of chromosome 21 is sufficient to cause many of the phenotypic features of Down syndrome. When mouse models of Down syndrome have been created, one of the models consisted of animals with an extra dose of the region of mouse chromosome 16 syntenic with human chromosome 21. These animals displayed a number of phenotypes, including deficits in learning and memory. The copy number of the YAC transgenes ranged from 1 to 3 copies per mouse genome, and suggested that there was a low level overexpression of the genes present on the YACs transgenic mice. Furthermore, RT-PCR analysis of at least one transcription unit on each one of the YACs suggested that the human genes were correctly transcribed in the foreign environment of the mouse genome, providing further evidence that the gene controlling Down syndrome and learning ability is located within the chromosome 21, region 21q22.2.

The only gene that was found to be present in the 180 kb telomeric region is DYRK. Expression studies confirmed that this gene was overexpressed as a result of the transgenesis with both the full length YAC 152F7 and the telomeric fragment, and that the level of overexpression was consistent with the copy number of the transgenes.

These findings show that correct dosage of the minibrain gene is crucial for normal development of the nervous system.

VI. Diagnostic and Therapeutic Utility of the Invention

Because of the severe consequences of Down syndrome, it is very important to diagnose this disease prenatally. By identifying the gene and the gene sequence responsible for Down syndrome, these findings are advantageously utilized to provide diagnostic test for detection of the Down syndrome trait prenatally.

For this purpose, the assay is provided comprising cDNA complementary to the gene region and/or region responsible for Down syndrome. Generally, using methods known in the art, the labeled diagnostic cDNA or RNA corresponding to the Down syndrome gene is brought in contact with cells or tissue of the diagnosed individual and both the DNA endogenous to the individual to be diagnosed and the diagnostic cDNA or RNA are subjected to hybridization and the presence of the complementary bases pairs complex is detected depending on the label by autoradiography, immunofluorescence or any other appropriate means which are known or will become known in the art. Useful technique for this assay includes dot-blot hybridization on extracted mRNA, described in *Mol. Cell Biol.*, 3:241 (1983).

The label may be radioactive, immunoreactive, fluorescent or any other label which would allow the detection of the presence of the formed hybridization product.

Typically the method of diagnosing Down's syndrome comprises step:

(a) manufacturing a genetic probe by producing a homologous DNA strand to the human DYRK gene;

(b) labeling said probe;

(c) exposing sample tissue to be diagnosed to the genetic probe;

(d) observing tissue for presence of three probes within a single nucleus.

The diagnosis is performed, preferably, in early months of pregnancy. When the test is positive, hybridization occurs and the presence of Down syndrome DNA is detected. When the test is negative, Down syndrome DNA is not detected.

The current invention is also useful for correction of Down syndrome using gene therapy, wherein the wild type DNA sequence is delivered, for example by homologous replacement to the cells of the Down syndrome patient and exchanged for the mutated Down syndrome sequence.

Such method for therapy for Down's syndrome patients mental retardation comprises steps:

(a) producing a homologous DNA sequence to the human DYRK gene;

(b) optionally attaching a transcription exclusion moiety to said strand;

(c) providing said sequence in a pharmaceutically acceptable carrier; and (d) treating said patients with a dosage which will disable the DYRK gene to the extent necessary to approximate normal DYRK gene expression levels.

Additionally, the invention concerns a method of producing a pharmaceutical composition for the treatment of Down's syndrome patient mental retardation comprising:

(a) producing DYRK gene product; and (b) developing an antagonist to the DYRK gene product.

EXAMPLE 1

Screening of Mice

This example describes procedures used for preparation and screening of generated transgenic mice.

Screening of mice was performed using PCR as described in *Genomics*, 27:425 (1995).

New primers for the delineation of the 152F7 YAC fragments were:

1032T
Forward: 5'-CATGTCCATAACATTTTTACGG-3'; (SEQ ID NO: 1)
Reverse: 5'-ATCGACATCTTG-GCAGTTGG-3', (SEQ ID NO: 2) anneal temperature 58° C.;
D21S394
H2-127-1: 5'-GGAGCCGGTTCTTC-GAAGG-3'; SEQ ID NO: 3
H2-127-2: 5'-CAGCGTCCGGAATTCCTGC-3' SEQ ID NO: 4
D21S270
AFM031xc5a: 5'-GAAATGTTTTAATAAATGGTGGTTA-3'; (SEQ ID NO: 5)
AFM031xc5m: 5'-ACAAAGTTATGGTCAAGGGG-3'; (SEQ ID NO: 6) anneal temperature 55° C. for preceding 2 primer sets.

EXAMPLE 2

Fluorescent In-Situ Hybridization

This example describes procedure used for fluorescence in situ hybridization.

Three colour FISH to interphase chromosomes was performed as described previously in *Hum. Mol. Genet.* 4:1903 (1995) with minor modifications. Probes were prepared from three different P1 clones mapping to each YAC by random priming labelling with biotin, digoxigenin or FITC. Alternatively, DOP-PCR generated YAC probes labelled with biotin or digoxigenin were also prepared and used.

Biotinylated, FITC- and digoxigenin-labelled probes were detected with avidin-CY5, a mouse antibody against FITC followed by a fluorescein labeled horse-anti-mouse antibody and rhodamine-labelled sheep-antidigoxigenin antibodies. Interphase cell preparation were made from 20–40 μl of peripheral blood drawn from the tail vein. Red blood cells were lysed in 0.85% ammonium chloride and white blood cells were subjected to hypotonic treatment in 75 mM KCl for 10–20 min. at 21° C. The cells were then dropped on pre-cleaned microscope slides and fixed in two changes of acidic acid: methanol (1:3, vol:vol).

EXAMPLE 3

Behavioral Tests

This example describes method used for behavioral testing.

All behavioral tests were done on two independent lines of full-length YAC transgenic animals. Where there were no significant differences between lines, the results were collapsed across this variable. This was true of all the probe tests performed as part of the Morris water maze. In the interests of circumspection, Dunnett's post-hoc correction employed all groups of animals used.

The YAC transgenic mice were created in the FVB background. These mice are blind, probably due to the recessive Pdeb mutation[12-14] which exists in the strain. As these animals consequently perform very poorly on the Morris maze, transgenic/FVB males were mated with C57/BL6 females to produce F1 hybrid males for behavior testing.

EXAMPLE 4

Morris Water Maze

This example describes Morris water maze testing.

The Morris maze described in *Learning and Motivation*, 12:239 (1981) was performed as described in *Science* 257:2061 (1992) except that the invisible platform training and probe test were followed by two days of training in which the hidden platform was switched to the opposite quadrant and this was in turn followed by a reverse probe test according to *Cell*, 81:811 (1995). Each training block represents four different trials, in which the mice were released in a pseudo-random fashion from each of the four quadrants of the swimming pool. Three blocks of trials were performed per day. The pool was 1.2 meters diameter, the distance of the pool from the walls of the room varied between 35 cm and 102 cm, the interior of the pool was painted white and the water was rendered opaque by the addition of white non-toxic powder paint. The platform was white in color, 14.5 cm in diameter and the surface of the platform was submerged 2 cm beneath the surface of the water. The visible flag wa 26.5 cm tall and 8.5 cm at its broadest.

The following numbers of animals were used in the water maze: 230E8 line A: 27; 230E8 line B: 23 for the visible platform and 19 for the remainder of the test; 141G6 line A: 17; 141G6 line B: 16; 152P7 line A: 23 for the visible platform and 19 for the remainder of the test; 152F7 line B: 21 for the visible platform and 19 for the remainder of the test; 152F7 tel: 24; 285E6 line A: 22; 285E6 line B: 15; non-transgenic: 47 for the visible platform and 45 for the remainder of the test.

There were no consistent significant differences between the swimming speeds of the different classes of animals tested in the water maze. The differences in performances on the test were not due to deficiencies in swimming ability. This was supported by the effective learning of the visible platform test by all classes of mice.

EXAMPLE 5

Spontaneous Locomotor Activity

This example describes spontaneous locomotor activity testing.

To measure spontaneous locomotor activity, the mice were placed in a box (47 cm long axis, x26 cm short axis, x15 cm high) for 1 h in the dark and monitored by eight equally spaced infra-red beams along the short axis.

The following numbers of animals were analyzed for activity: 152F7 line A: 23; 152F7 line B: 18; 152F7 tel: 24; non-transgenic: 44.

EXAMPLE 6

Histopathology

This example describes histopathological methods.

YAC transgenic and non-transgenic mice (FVB background: 230E8 n=5; 141G6 n=8; 152F7 n=9; 285E6 n=4, nor-transgenic n=5; age=54.1±2.85 weeks (mean±SEM)) were fixed by whole body perfusion through the left ventricle using Bouin's solution, sectioned and mounted for microscopic examination.

Vectabond-treated glass slides were used to mount 5 to 10 μm sections. The sections were air-dried overnight, deparaffinized and hydrated via xylenes and alcohols to water. Sections were stained with LFB-CV or H&E.

Immunohistochemistry for GFAP employed pretreatment of slides with 3% $H_2O_2$ in methanol to block staining by endogenous peroxidases. To expose epitopes, slides were boiled in water for 15 min using a microwave oven and cooled to room temperature. All subsequent steps were performed at this temperature. The slides were rinsed three times in 0.1 M phosphate buffered saline (PBS) for 5 min each. After incubation in 0.4% Triton X-100 (TX-100) in 0.1 M PBS for 5 min, the slides were blocked by transferring them for 1 hour to blocking solution (10% normal horse or goat serum in 1% bovine serum albumin dissolved in 0.1% TX-100/0.1 M PBS).

The slides were then incubated for 24 h in primary antibody to GFAP (Boehringer), diluted in blocking solution lacking bovine serum albumin, washed in 0.1 M PBS, incubated in biotin conjugated secondary for 2 to 4 h, and incubated in avidin conjugated horseradish peroxidase for 30 min. After rinsing in 0.1 M PBS, the slides were colour developed by reacting with 0.05% diaminobenzidine in 0.01% $H_2O_2$. The slides were then rinsed in 0.1 M PBS, dehydrated through graded ethanols to xylenes and cover slipped.

Analysis of cortical neuronal density was performed by counting the neurons in ×50 microscopic fields of H&E stained sections of cerebral cortex at the level of the caudate nucleus. The neurons were counted blind using NIH Image, version 1.6. For each mouse, five sections were counted and the mean value of the five sections used in the statistical analysis. Thus, the number of independent samples is equivalent to the number of mice employed, resulting in a conservative statistical analysis.

EXAMPLE 7

Electrophysiological Testing

This example describes a method used for electro physiological testing.

Long-term electrophysiological potentiation was examined in the CA1 region of 400 μm thick hippocampal slices using techniques described in Cell, 81:891 (1995).

EXAMPLE 8 cDNA Selection

This example describes procedures used for selection of cDNA clones. cDNA clones that mapped to YAC 152F7 were isolated using P1 clones that mapped to this YAC. The P1 clones were employed in cDNA selection performed as described in Genomics, 23:75 (1994).

The GenBank accession for the utilized cDNA sequences are U69115 (21ES0227) and U69119 (21ES0291).

EXAMPLE 9

Reverse Transcriptase—Polymeric Chain Reaction

This example describes methods used for RT-PCR.

RT-PCR was performed as described in Genomics, 27:425 (1995). The primers for PCR detection of minibrain transcripts were:

mnbxn7 (13: 5'-GTGCATTTGAAACGC-CACTT-3'; (SEQ ID NO: 7)

rl: 5'-CCAACTGACAAGA(A/G)CTGCCA-3') (SEQ ID NO: 8).

The mouse and human transcripts were distinguished by subsequent Sau3AI digestion, the mouse product being 280 bp and the human being 196 bp. Equal loading of samples was controlled for using primers that recognize the housekeeping genes GdX described in Genomics, 7:453 (1990). (GdXxn3-4 f4: 5'-GGCAGCTGATCTCCAAA-GTCCTG-3' (SEQ ID NO: 9);

r4: 5'-AACGTTCGATGTCATCCAGTGTTA-3') (SEQ ID NO: 10) and G3PDH.

The GdX primers cross an intron and therefore give different size PCR products from genomic DNA (241 bp) and cDNA (126 bp). Quantitation of RT-PCR was as described in Genomics, 27:425 (1995).

EXAMPLE 10

Genes Contained in YAC 152F7

This example describes conditions used for detection of genes contained in YAC 152F7.

To identify candidate genes for the behavioral defects of the 152F7 mice magnetic bead capture to isolate fetal brain cDNAs that map to the YAC was used. Sequence obtained from these clones revealed that two of the cDNAs (21ES0227 and 21ES0291) deposited at gen Bank under accession numbers U69115 and U69119 respectively and one previously isolated cDNA (21ES0034), were human homologs of the Drosophila minibrain (mnb) gene (blastin, P(N)<1e-180; blastx, P(N)<1e-73).

What is claimed is:

1. In a method for prenatal testing of a child, the improvement comprising testing for Down syndrome, comprising the steps of:

(a) preparing nucleic acid probes which hybridize to the human DYRK gene;

(b) labeling said probes so as to make their presence in a cell detectable;

(c) obtaining cells from said child;

(d) exposing said cells to said probes; and (e) detecting specific binding of three probes in a single nucleus of a cell.

2. The method of claim 1 wherein the probe is radiolabelled, immunolabelled or labeled with fluorescence.

* * * * *